United States Patent [19]
Au et al.

[11] Patent Number: 5,908,943
[45] Date of Patent: Jun. 1, 1999

[54] PROCESS FOR PREPARATION OF EPOXY COMPOUNDS ESSENTIALLY FREE OF ORGANIC HALIDES

[75] Inventors: Andrew T. Au, Sugarland; J. Lowell Nafziger, Lake Jackson, both of Tex.

[73] Assignee: The Dow Chemical Company, Midland, Mich.

[21] Appl. No.: 08/731,215

[22] Filed: Oct. 8, 1996

Related U.S. Application Data

[62] Division of application No. 08/363,129, Dec. 23, 1994, Pat. No. 5,578,740.

[51] Int. Cl.⁶ .................................................. C07D 303/22
[52] U.S. Cl. ........................... 549/559; 549/560; 525/502; 528/159
[58] Field of Search ........................... 525/502; 528/159; 549/559, 560

[56] References Cited

U.S. PATENT DOCUMENTS

| | | | |
|---|---|---|---|
| 4,507,492 | 3/1985 | Woo | 560/64 |
| 4,544,731 | 10/1985 | Cavitt et al. | 528/89 |
| 4,740,330 | 4/1988 | Wang et al. | 260/395 |
| 4,754,003 | 6/1988 | Monnier et al. | 525/490 |
| 4,810,776 | 3/1989 | Karlhuber et al. | 528/488 |
| 4,831,101 | 5/1989 | Jellinek et al. | 528/87 |

FOREIGN PATENT DOCUMENTS

| | | |
|---|---|---|
| 0 368 421 | 5/1990 | European Pat. Off. . |
| 0 370 946 A2 | 5/1990 | European Pat. Off. . |

*Primary Examiner*—Ba K. Trinh

[57] ABSTRACT

Epoxy-containing compounds which are essentially free of organic halides are prepared by (I) reacting an allyl derivative of an active hydrogen-containing compound with (II) a peroxygen-containing compound. The epoxy-containing compounds are useful in coatings, castings, laminates etc.

8 Claims, No Drawings a patent document

PROCESS FOR PREPARATION OF EPOXY COMPOUNDS ESSENTIALLY FREE OF ORGANIC HALIDES

CROSS-REFERENCE TO RELATED APPLICATION

This application is a division of application Ser. No. 08/363,129 filed Dec. 23, 1994, now U.S. Pat. No. 5,578,740.

FIELD OF THE INVENTION

The present invention pertains to a process for the preparation of epoxy-containing compounds which are essentially free of organic halides.

BACKGROUND OF THE INVENTION

It is well known to prepare epoxy compounds by reacting epihalohydrin with an active hydrogen-containing compound and subsequently dehydrohalogenating the chlorohydrin intermediate product with a basic acting compound such as an alkali or alkaline earth metal hydroxide or carbonate. Since epichlorohydrin is prepared in three steps from propylene (the very basic starting material) this entire process for the preparation of glycidyl ether (or other glycidyl derivative) based epoxy resins involves four or five steps depending upon whether or not steps four and five are conducted simultaneously or separately. The five-step reaction is as follows:

1) propylene+chlorine → allyl chloride
2) allyl chloride+water+chlorine → dichloropropanol
3) dichloropropanol+NaOH → epichlorohydrin
4) epichlorohydrin+active hydrogen-containing compound such as a bisphenol → chlorohydrin intermediate
5) chlorohydrin intermediate+basic acting compound → glycidyl ether epoxy resin In the four-step reaction, steps four and five are conducted essentially simultaneously.

The most widely used current processes for the preparation of epichlorohydrin also produce a significant amount of chlorinated by-product such as 2-chloropropene, 2-chloropropane, allyl chloride, 1,2-dichloropropane, 3,3-dichloropropene, 2,3-dichloropropene, 1,3-dichloropropene, 1,3,3-trichloropropene, 1,2,3-trichloropropane, bis-(dichloropropyl)ethers, 2,3-dichloro-1-propanol, 1,3-dichloro-2-propanol. These by-products must be sold into a useful market or disposed of by environmentally friendly methods. Moreover, certain of the by-products are difficult to separate from the epihalohydrin. When the epihalohydrin is used to make epoxy resin, the epoxy resin becomes contaminated with undesirable bound and hydrolyzable halides resulting from reaction by-products and from incompletely reacted epihalohydrin.

What is needed is a process to make similar epoxy resins or other glycidyl compounds which process has one or more of the following advantages: fewer process steps, fewer halogenated by-products, and/or lower levels of halogenated contaminants, by-products, in the resulting resin or compound or simultaneously having an epoxide equivalent weight less than about 200 and an amount of total organic halide of less than about 200 ppm excluding any halogen atoms attached to an aromatic ring to which the group containing the vicinal epoxide group is attached.

SUMMARY OF THE INVENTION

The process of the present invention meets at least one of the foregoing advantages and preferably meets all of them.

One aspect of the present invention is a process to make an epoxide compound comprising the steps of (1) providing an allyl reagent which is substantially halogen-free and which reacts with an acid, hydroxyl or amine group to form an allyl ether, allyl thioether, allyl ester or allyl amine;

(2) allylating one or more compounds containing at least one active hydrogen atom using the allyl reagent from step (1), whereby allyl ether, allyl thioether, allyl ester or allyl amine compound is formed; and (3) converting the allyl groups on the compound from step (2) to epoxide groups, whereby a glycidyl ether, glycidyl thioether, glycidyl ester or glycidyl amine compound is formed.

A second aspect of the present invention is a glycidyl ether, glycidyl thioether, or glycidyl ester compound made by the above defined process which compound has an epoxide equivalent weight of less than about 300, preferably less than about 220, more preferably less than about 185 and contains no more than about 300 or 150, preferably less than about 50, more preferably less than about 30, most preferably less than about 10 ppm total organic halide excluding any any halogen atoms attached to an aromatic ring to which the group containing the vicinal epoxide group is attached.

A third aspect of the present invention is an improvement in a process to make an allyl ether, allyl thioether, allyl ester or allyl amine comprising the step of reacting a compound containing at least one hydroxyl, thiol, ester or amine group with a compound containing an allyl carboxylate group or an allyl carbonate group in the presence of a metal catalyst; wherein said improvement resides in conducting the reaction in the presence of a catalyst selected from the group consisting of ruthenium, rhodium, rhenium, palladium, iridium, tungsten, molybdenum, chromium, platinum, nickel, tin, copper, osmium, iron, or any combination thereof either as the free metal or as salts thereof in an amount of from about 0.05 to about 200 mmoles per mole of active hydrogen atom contained in the compound(s) containing active hydrogen atom(s).

A still further aspect of the present invention pertains to a resin having an average of more than one vicinal epoxide group per molecule and an amount of total organic halide of less than about 300 or 150, preferably less than about 50, more preferably less than about 30, most preferably less than about 10 ppm excluding any halogen atoms attached to an aromatic ring to which the group containing the vicinal epoxide group is attached.

Using the present invention, the ultimate production of the epoxy-containing compounds can be accomplished efficiently in high yields in three steps starting from the basic raw material, propylene; whereas the prior art process involves four or five steps starting from the basic raw material propylene. The three-step process is summarized as follows:

1) Propylene+oxygen+acetic acid+catalyst → allyl acetate;
2) Allyl acetate+active hydrogen-containing compound such as a bisphenol → diallyl derivative of active hydrogen-containing compound; and
3) Diallyl derivative of active hydrogen-containing compound+peroxy oxidant → diglycidyl derivative of active hydrogen-containing compound. Although acetic acid is illustrated above to prepare allyl acetate which is employed as the allylating agent, it is understood that other acids and allylating agents as enumerated elsewhere herein can be employed in the process of the present invention.

Further, the compounds prepared by the process of the present invention have none or very little total organic halides present when the active hydrogen-containing compound is free of organic halides. The process of the present invention is suitable for the preparation of the diglycidyl ether of tetrabromobisphenol A; however, it will not be essentially free of organic halides because of the bromine present in the tetrabromobisphenol A starting material. It will however, be essentially free of any halides which would have been present had the process involving epichlorohydrin been employed. Epoxy resins which contain none or very little total organic halides are particularly suitable for electronic applications, metal primer coatings, cathodic electrodeposition coatings, powder coatings, and the like.

The present invention can comprise, consist of, or consist essentially of, all or only a portion of the aforementioned components or reaction steps. Components or reaction steps can be eliminated singly or in multiples of any two or more.

The compositions, products or process of the present invention can be free of any component not specifically enumerated when and if desired. Also, the present invention can be free of any component, compound or process step even though such was orginally believed to be a part of the invention.

DETAILED DESCRIPTION OF THE INVENTION

Definitions

By the term "compound containing an active hydrogen atom" or "active hydrogen-containing compound", it is meant that: (1) the compound is reactive with an allyl carboxylate such that the allyl derivative of the compound containing an active hydrogen atom is produced; or (2) the compound is reactive with an allyl carbonate such that the allyl derivative of the compound containing an active hydrogen atom is produced.

By the term "epoxy-containing compound", it is meant a compound containing one or more vicinal epoxide groups per molecule.

By "essentially free of organic halogen" it is meant that the epoxy resin or epoxide-containing product contains less than about 300, preferably less than about 150 and more preferably less than about 50 and most preferably less than about 10 ppm by weight of total organic halogen atoms (hydrolyzable halide and bound halide).

By "hydrolyzable halide", it is meant a relatively labile halide which is attached to a carbon atom activated by an adjacent functional group (such as carbonyl, carboxyl, beta-hydroxyl group, etc.), particularly a chlorohydrin,

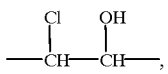

group.

By "bound halide", it is meant a relatively inert halide which is not activated by an adjacent functional group.

By "total organic halide", it is meant the combined amount of "hydrolyzable halide" and "bound halide".

The term "hydrocarbyl" as employed herein means any aliphatic, cycloaliphatic, aromatic, aryl substituted aliphatic or cycloaliphatic, or aliphatic or cycloaliphatic substituted aromatic group. Likewise, the term "hydrocarbyloxy" means a hydrocarbyl group having an oxygen linkage between it and the carbon atom to which it is attached. The term "divalent hydrocarbyl group" refers to the aforementioned hydrocarbyl groups minus an additional hydrogen atom.

The term "catalyst efficiency" or "turnover rate" is defined by the following equation:

$$\text{Catalyst Efficiency or Turnover Rate} = \frac{(\text{Moles Product Formed/Mole of Catalyst})}{\text{Unit of Time}}$$

NUMERICAL VALUES RECITED HEREIN

Any numerical values recited herein include all values from the lower value to the upper value in increments of one unit provided that there is a separation of at least 2 units between any lower value and any higher value. As an example, if it is stated that the amount of a component or value of a process variable such as, for example, temperature, pressure, time and the like is, for example, from 1 to 90, preferably 20 to 80, more preferably from 30 to 70, it is intended that values such as 15 to 85, 22 to 68, 43 to 51, 30 to 32 etc. are expressly enumerated in this specification. Usually, for values which are less than one, one unit is considered to be 0.1; therefore, the minimum separation between any lower value and any higher value is 0.2. However, for the amounts of catalysts, one unit is considered to be 0.001, 0.01, 0.1 or 1 as appropriate. These are only examples of what is specifically intended, and all possible combinations of numerical values between the lowest value and the highest value enumerated are to be considered to be expressly stated in this application in a similar manner.

ALLYL REAGENT

The allyl reagent is preferably an allyl carboxylate or an allyl carbonate, and is more preferably an allyl carboxylate, and most preferably, it is allyl acetate.

The allyl reagent is employed in amounts such that the equivalent ratio of allyl reagent to active hydrogen atom contained in the active hydrogen-containing compound is from about 0.1:1 to about 500:1, preferably from about 0.5:1 to about 5:1, more preferably from about 1:1 to about 1.5:1. At ratios significantly above 1:1, the excess allyl reagent is being primarily employed as a solvent rather than as a reactant.

At ratios below about 0.1:1, the conversion to the desired product is very low and the excess active hydrogen-containing reactant must be recovered and recycled in the process.

ALLYL CARBOXYLATES

The allyl carboxylates from which the allyl derivatives of active hydrogen-containing compounds can be prepared include, but are not limited to, for example, those represented by the following formula XI or any combination of any two or more such allyl carboxylates:

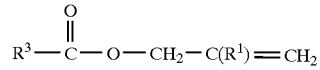

Formula XI wherein $R^1$ is hydrogen or an alkyl group having from 1 to about 4 carbon atoms, and $R^3$ is hydrogen or an alkyl, cycloalkyl or aryl group having from 1 to about 10 carbon atoms. Preferably, the allyl carboxylate is allyl formate, allyl acetate, allyl propionate, allyl benzoate, and diallyl carboxylates such as oxalate, glutarate, succinate, or any combination thereof and the like. Most preferred as the allyl carboxylate is allyl acetate.

PREPARATION OF ALLYL CARBOXYLATES

Certain useful allyl carboxylates such as allyl acetate and methallyl acetate are commercially available. Others can be prepared by the oxidation of propylene in the presence of oxygen, a carboxylic acid (such as formic acid, acetic acid or propionic acid) and a palladium catalyst as described in U.S. Pat. No. 3,970,713 which is incorporated herein by reference. The reaction is conducted at temperatures of from about 50° C. to about 250° C. In the reaction, from about 5 to about 20 moles of water per mole of acid, from about 1 to about 5 moles of oxygen per mole of acid and from about 4 to about 40 moles of propylene per mole of oxygen are employed. This reaction proceeds readily in one step from the propylene to the allyl carboxylate without the use or production of halogenated materials.

ALLYL CARBONATES

Suitable allyl carbonates which can be employed herein include, for example, those represented by the following formula XII

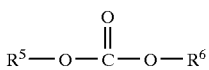

Formula XII wherein $R^5$ is

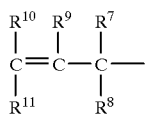

wherein $R^6$ is $R^5$ or a hydrocarbyl radical of up to about 20 carbon atoms, preferably from 1 to about 10, more preferably from 1 to about 4 carbon atoms; $R^7$–$R^{11}$ are each independently hydrogen or a hydrocarbyl group having up to about 20 carbon atoms, preferably from 1 to about 10, more preferably from 1 to about 4 carbon atoms. Particularly suitable allyl carbonates which can be employed include, for example, diallyl carbonate, dimethallyl carbonate, methyl allyl carbonate, ethyl allyl carbonate, allyl phenol carbonate, or any combination of any two or more of such allyl carbonates and the like.

PREPARATION OF ALLYL CARBONATES

The allyl carbonates can be prepared by reacting dimethyl carbonate or phosgene with allyl alcohol. For example, allyl methyl carbonate or diallyl carbonate can be generated by reacting at room temperture or below allyl alcohol with dimethyl carbonate in the presence of a catalytic amount of base such as sodium hyroxide, sodium hydride or sodium methoxide, distilling out methanol being formed during the process. Allyl methyl carbonate and/or diallyl carbonate prepared in this manner is suitable as the allylation agent.

PREPARATION OF THE ALLYL DERIVATIVE OF ACTIVE HYDROGEN-CONTAINING COMPOUNDS

The allyl derivative of the active hydrogen-containing compound is prepared by reacting an active hydrogen-containing compound with an allyl carboxylate as the allylating agent in the presence of a catalyst, optionally but preferably in the presence of at least one complexing agent for the catalyst and optionally but preferably in the presence of at least one base compound and further optionally but preferably in the presence of one or more suitable solvents.

The reaction is conducted at a temperature of from about 0° C. to about 200° C., preferably from about 60° C. to about 150° C., more preferably from about 60° C. to about 110° C., at a pressure sufficient to keep the reaction mixture in liquid form for a time sufficient to essentially complete the reaction, usually for from about 0.1 to about 72, preferably from about 0.1 to about 48, more preferably from about 0.1 to about 24, hours. Higher temperatures require shorter reaction times, whereas lower temperatures require longer reaction times. Optimum temperature and times for particular reactants will vary depending upon the reactivity of the particular reactants, solvents and catalysts employed; however, such optimum temperatures and times can readily be determined in the laboratory with minimum effort.

At temperatures below about 0° C., the reaction proceeds at a slower rate.

At temperatures above about 200° C., costs for providing the increased temperature are incurred.

Particular pressures are not deemed to be determinative of any appreciative affects on the process; however, pressures should be employed which preferably will keep the reaction in the liquid phase.

When alkali or alkaline earth metal hydroxides, hydrides, alkoxides bicarbonates or carbonates are employed as the base material, the corresponding metal carboxylate is formed as a by product which can readily be removed by water washing, filtration, decantation, centrifugation or any combination thereof and the like.

When an amine compound is employed as the base material, an amine salt of the carboxylate is formed as a by product which can readily be removed by water washing, decantation, filtration, centrifugation or any combination thereof and the like.

The allyl derivatives can, if desired, be recovered from the reaction mixture by any suitable means. A particularly suitable means is, for example, by the following:
  when a heterogeneous catalyst is employed by:
    1) adding water to dissolve the carboxylate salt, then
    2) removing the catalyst by filtration, decantation, centrifugation or any combination thereof, then
    3) separating the organic layer from the aqueous layer by decantation or the like, and finally
    4) removing all volatiles from the organic layer to recover the product as a bottom product by distillation, or evaporation.
  when a homogeneous catalyst is employed by:
    1) adding water to dissolve the carboxylate salt, then
    2) separating the organic layer from the aqueous layer by decantation, then
    3) removing all volatiles and catalyst to recover the product as a bottom product by distillation.

The allyl derivative of the active hydrogen-containing compound can also be prepared by reacting an active hydrogen-containing compound with an allyl carbonate as the allyl reagent in the presence of a catalyst such as, for example, ruthenium, rhodium, rhenium, palladium, molybdenum, tungsten, nickel, platinum, or any combination thereof and the like; and optionally in the presence of one or more suitable solvents. Suitable reaction temperatures are from about −20° C. to about 250° C., preferably from about 20° C. to about 200° C., more preferably from about 30° C. to about 120° C. The reaction time will vary with the temperature and the particular catalyst and amount of catalyst employed; however, suitable reaction times include from about 0.1 to about 100, preferably from about 0.5 to about 50, more preferably from about 1 to about 10 hours. This process employing phenols, thiophenols and aryl amines as the active hydrogen-containing compound is described by Edmund P. Woo in U.S. Pat. No. 4,507,492 which is incorporated herein by reference in its entirety. The process employing carboxylic acids as the active hydrogen-containing compound is described by Edmund P. Woo in U.S. Pat. 4,362,670 which is incorporated herein by reference in its entirety.

The allyl derivatives can be recovered from the reaction mixture at or above the temperature required to remove the solvent. Generally, the recovery is accomplished at temperatures of from about 0° C. to about 200° C., preferably from about 25° C. to about 250° C., more preferably from about 25° C. to about 200° C. with or without reduced pressure as appropriate.

Suitable allyl derivatives which can be prepared in the process of the present invention include but are not limited to, for example, those represented by any one of the following formulas I, II, III, IV, V, VI or VII $$R^2-Z \qquad \text{Formula I}$$

$$Z-R^2-Z \qquad \text{Formula II}$$

Formula III
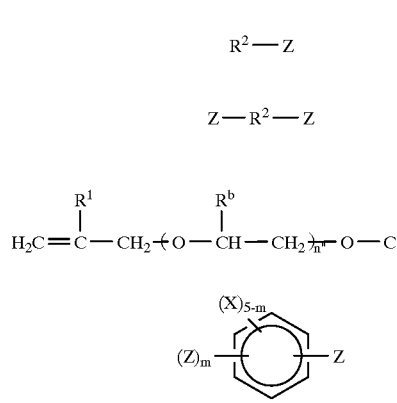

Formula IV
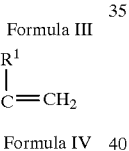

Formula V
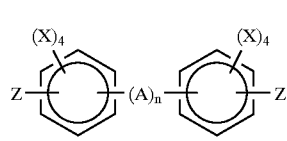

Formula VI
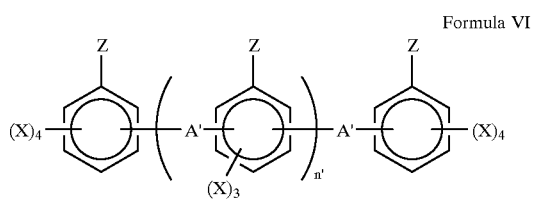

Formula VII
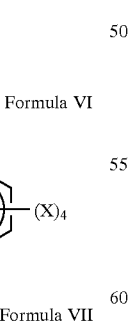

Formula VIII
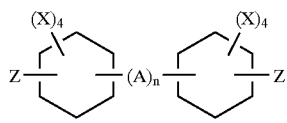

Formula IX
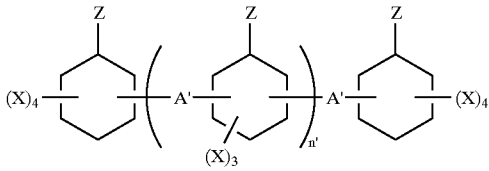

wherein each A is independently a divalent hydrocarbyl group having from 1 to about 20, preferably from 1 to about 10, more preferably from 1 to about 4 carbon atoms, —O—, —S—, —S—S—, —SO— or —SO$_2$—, —CO—, —COO—, —C=CR—, —C—O—C—, CHX$^a$ (X$^a$ is a halogen, cyanide and the like); A' is a divalent hydrocarbyl group having from 1 to about 8, preferably from 1 to about 4, more preferably from 1 to about 2 carbon atoms; each X is independently a monovalent hydrocarbyl or hydrocarbyloxy group having from 1 to about 20, preferably from 1 to about 10, more preferably from 1 to about 4 carbon atoms, a halogen atom (preferably chlorine or bromine), or a —NO$_2$ group; each Z is independently a

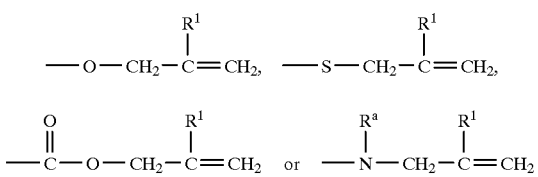

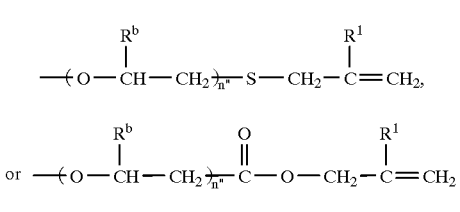

group; R$^a$ is hydrogen, an alkyl group having from 1 to about 4 carbon atoms or a —CH$_2$—C(R$^1$)=CH$_2$ group; R$^b$ is hydrogen or an alkyl group having from 1 to about 2 carbon atoms; R$^1$ is hydrogen or an alkyl group having from 1 to about 4 carbon atoms; R$^2$ is a monovalent or divalent aliphatic or cycloaliphatic hydrocarbon group having from about 2 to about 20, preferably from about 3 to about 10 more preferably from about 4 to about 8 carbon atoms; m has a value of zero or 1; n has a value of zero or 1; n' has a value from 0.01 to 10, preferably from about 0.5 to about 6, more preferably from about 1 to about 4; n' has a value from zero to about 50, preferably from about zero to about 20, more preferably from about zero to about 6.

ACTIVE HYDROGEN-CONTAINING COMPOUNDS

The active hydrogen-containing compound preferably contains at least one hydroxyl group, thiol group, primary or secondary amine group or carboxylic acid group. It more preferably contains on average more than one such group, and most preferably contains on average at least about 1.8 such groups. It preferably contains no more than about 10 such groups. It more preferably contains hydroxyl or carboxylic acid groups, and most preferably contains hydroxyl groups. Examples of suitable active hydrogen-containing compounds include mono-, di- or multi-functional aliphatic, cycloaliphatic or aromatic hydroxyl-containing; thiol-containing; primary and secondary aromatic amine-containing; carboxyl-containing compounds or any combination of such compounds and the like. Particularly suitable examples of active hydrogen-containing compounds include those represented by any one of Formulas I, II, III, IV, V, VI, VII, VIII or IX and the following Formula X Formula X

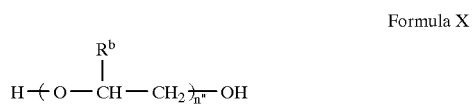

or any combination of any two or more such active hydrogen-containing compounds wherein A, A', $R^a$, $R^b$, $R^1$, $R^2$, X, m, n, n' and n'' are as defined above and Z is —OH, —SH, —COOH; —NH$_2$, or —NH($R^4$), wherein $R^4$ is hydrogen or a saturated or unsaturated aliphatic group having from 1 to about 20, preferably from 1 to about 10, more preferably from 1 to about 4 carbon atoms.

HYDROXY-CONTAINING COMPOUNDS

The hydroxyl-containing compounds can be aliphatic, cycloaliphatic or aromatic compounds.

Particularly suitable aromatic hydroxyl-containing compounds include, for example, phenol, cresol, anisole, bis-hydroxyphenyl, catechol, resorcinol, bisphenol A (p,p'-isopropylidene diphenol), bisphenol F (p, p'-methylene diphenol), bisphenol K (p,p'-diphenolcarbonyl), dihydroxy-α-methylstilbene, dihydroxy biphenyl, bis(hydroxyphenyl) fluorene, phenol-aldehyde novolac resins, alkyl substituted phenol-aldehyde novolac resins, or any combination thereof and the like. Preferred aromatic hydroxyl-containing compounds include, for example, bisphenol A, bisphenol F, dihydroxy-α-methyl-stilbene, phenol-formaldehyde novolac resins, cresol-formaldehyde novolac resins or any combination of any two or more of such compounds thereof and the like.

The active hydrogen-containing compound is preferably a bisphenol, and is most preferably bisphenol A.

Suitable aliphatic hydroxyl-containing compounds include, for example, methanol, ethanol, propanol, butanol, hexanol, octanol, butanediol, hexanediol, octanediol, polyoxyalkylene glycols having a weight average molecular weight of from about 106 to about 10,000, preferably from about 106 to about 2,000, more preferably from about 106 to about 1,000, or any combination thereof.

Particularly suitable cycloaliphatic hydroxyl-containing compounds include, for example, cyclopentanol, cyclohexanol, methylcyclohexanol, dihydroxy cyclohexane, norbornanediol, cyclohexanedimethylol, dicyclopentadienediol, vinylcyclohexene derived diols, or any combination thereof.

THIOL COMPOUNDS

Particularly suitable thiol compounds include, for example, thiophenol, bisthiophenol, thiobisphenol A, thiophenol-formaldehyde novolac resins, thiocresol-formaldehyde novolac resins, thionaphthol, or any combination of any two or more compounds thereof and the like.

CARBOXYL-CONTAINING COMPOUNDS

Particularly suitable carboxyl-containing compounds include, for example, aromatic mono-, di- and tri-carboxylic acids such as, for example, benzoic acid, phthalic acid, terephthalic acid; aliphatic mono and di-carboxylic acids such as, for example, acrylic acid, methacrylic acid, malonic acid, glutaric acid, succinic acid, cyclohexane dicarboxylic acid, or any combination of any two or more of such acids thereof and the like.

PRIMARY AND/OR SECONDARY AROMATIC AMINE-CONTAINING COMPOUNDS

Particularly suitable primary or secondary aromatic amine-containing compounds include, for example, aryl amines, such as, for example, diaminobenzene, aniline, N-methyl aniline, methylene dianiline, hydroxy-aniline, bis-aniline, diaminotoluene, amino-naphthylene or any combination thereof and the like.

BASE COMPOUNDS

It is theorized, without intending to be bound by such theory, that the base compounds facilitate the reaction by generating an anion from the hydroxy-containing compounds which will then be allylated by an allyl carboxylate- or allylcarbonate-metal complex to form the desired allyl products. The base compound is preferably any heterogeneous or homogenous compound or resin which removes a hydrogen atom from the active-hydrogen-containing compound under reaction conditions.

Suitable base compounds include, for example, alkali and alkaline earth metal bicarbonates, carbonates, hydroxides or hydrides or alkoxides, such as, for example, sodium carbonate, potassium carbonate, lithium carbonate, calcium carbonate, sodium hydroxide, potassium hydroxide, lithium hydroxide, calcium hydroxide, sodium bicarbonate, potassium bicarbonate, lithium bicarbonate, calcium bicarbonate, or any combination of any two or more such base compounds and the like. Particularly suitable base compounds include, for example, potassium carbonate, sodium carbonate, potassium hydroxide, sodium hydroxide, or any combination of any two or more such base compounds and the like. Preferred base compounds include, sodium carbonate and sodium hydroxide.

Suitable resinous bases include, for example, the hydroxide, quaternary ammonium or amino form of ion exchange resins, particularly styrene/divinyl benzene based ion exchange resins.

The base compounds are employed in amounts of from about zero to about 10, preferably from about 0.5 to about 2.0, more preferably from about 1.0 to about 1.2 equivalents per active hydrogen of the material to be allylated.

BUFFERING AGENTS

If desired, when water is employed as a solvent, either as the sole solvent or as a cosolvent, the strong base compounds such as hydroxides-or alkoxides can be modified with buffering agents such as, for example, alkali or alkaline earth metal bicarbonates, carbon dioxide, alkali or alkaline earth metal hydrogen phosphates, or alkali or alkaline earth, metal borates sodium carbonate or bicarbonate. Preferred is the formation of sodium carbonate in situ using sodium hydroxide and carbon dioxide. The buffering agents are employed in amounts such that the pH of the reaction mixture is from about 7 to about 13, preferably from about 8 to about 12, more preferably from about 9 to about 11. Usually, the amounts are from about 0.1 to about 10, preferably from about 1 to about 5, more preferably from about 1.1 to about 1.5 moles of buffering agent per mole of base compound.

CATALYSTS

Suitable catalysts include, for example, rhodium, ruthenium, rhenium, palladium, iridium, tungsten, molybdenum, chromium, platinum, nickel, tin, copper, osmium, iron, either as the free metal or as their salts such as, for example, carboxylates, halides, oxides, nitrates, sulfates, or any combination of any two or more of such metals or their salts and the like. The preferred catalysts include palladium, platinum, tin, tungsten, or any combination of any two or more of such catalysts or their acetate, chloride, nitrate or sulfate salts and the like. The most preferred catalysts are palladium and its salts such as its acetate, chloride, nitrate, sulfate salts and the like.

When the catalyst is employed in its free metal state it is preferably supported on a support material such as, for example, carbon, charcoal, activated charcoal, silica, alumina, zeolite, clay or any combination of any two or more of such support materials.

When the catalyst is in the form of a salt, it is preferably not supported.

The catalysts are employed in amounts, excluding support material, of from about 0.01 to about 200, preferably from about 0.1 to about 50, more preferably from about 0.1 to about 10, most preferably from about 0.5 to about 5 mmoles per active hydrogen atom contained in the active hydrogen-containing compound.

The supported catalyst contains from about 0.1 to about 80, preferably-from about 0.5 to about 50, more preferably from about 0.5 to about 10 percent by weight catalyst and from about 99.9 to about 20, preferably from about 99.5 to about 50, more preferably from about 99.5 to about 90 percent by weight support material.

When the catalyst is employed as a supported, heterogeneous catalyst, the reaction can be conducted in a fixed bed or suspended in the liquid reaction mixture.

COMPLEXING AGENTS

Complexing agents are preferably employed to serve as ligands to stabilize and to enhance the activity of the metal catalyst. The catalyst can be complexed with the complexing agent prior to addition to the reaction mixture or the catalyst complex can be formed in situ by adding the catalyst and the complexing agent separately to the reaction mixture.

Suitable complexing agents include, for example, organic mono- or di-phosphines, organic phosphites, organic stibines, oximes, organic arsines, diamines, and dicarbonyl compounds or any combination of any two or more base compounds and the like. Particularly suitable complexing agents include, for example, triphenyl phosphine, tris-p-tolyl phosphine, diphenylmethyl phosphine, diphenylphosphino ethane, or any combination of any two or more such complexing agents and the like. The preferred complexing agents include, tris-p-tolyl phosphine, triphenyl phosphine and diphenylphosphino ethane with triphenyl phosphine being most preferred.

Aqueous soluble complexing agents such as sulfonated triphenylphosphine may also be used. This type of ligand will have the advantage of being water soluble and easily washed out/separated from the organic product layer. Suitable sulfonated ligands include mono, di- or tris-metal salts of 3,3',3"-phosphinidynetris(benzenesulfonic acid) (metal= Na, K, Li or ammonium).

The complexing agents are employed in amounts of from about 10 to about 1000, preferably from about 50 to about 500, more preferably from about 200 to about 400 mole percent based upon the catalyst excluding any support material.

SOLVENTS

Suitable solvents which can optionally, but preferably, be employed in the process of the present invention include, for example, water, excess amounts of allyl carboxylate, oxygenated hydrocarbons (such as alcohols, ethers, glycols, glycol ethers, esters, ketones). Other solvents including nitro-alkanes, cyanoalkanes, alkyl sulfoxides, amides, aromatic hydrocarbons, halogenated hydrocarbons or any combination of any two or more such solvents and the like can also be used. Particularly suitable solvents include, for example, water, allyl acetate, acetonitrile, acetone, methyl ethyl ketone, ethyl acetate, dimethylformamide, dimethylsulfoxide, nitromethane, tetrahydrofuran, ethanol, isopropanol, glymes or any combination thereof and the like. The preferred solvents are water, allylacetate, isopropanol, acetone, acetonitrile, glycols and glycol ethers or any combination of any two or more such solvents and the like.

The solvents are employed in amounts of from about zero to about 100 preferably from about 0.5 to about 20, more preferably from about 1 to about 10 parts by weight based upon the weight of active hydrogen-containing component.

While it is not desired to be held to this theory, it is believed that when water is employed as a solvent, either as the sole about or as a cosolvent, that the base compound reacts with the active hydrogen-containing compound forming an ionized salt prior to reaction with the allylating agent. Therefore, it is believed that, if desired, the active hydrogen-containing compound can be prereacted with the base compound prior to being placed into contact with the allylating agent.

EPOXIDATION

The allyl ether, allyl thioether and allyl ester derivatives are converted to epoxy compounds by the methods known in the art for epoxidizing ethylenic or olefinic double bonds with peroxygen compounds. Suitable methods include those disclosed in *HANDBOOK OF EPOXY RESINS,* 1967, Lee and Neville, McGraw-Hill Book Co., Chapter 3; and *EPOXY RESINS Chemistry and Technology,* 2nd Ed., 1988, Clayton A. May, Marcel Dekker, Inc., Chapter 2, part III, pp. 15–46, both of which are incorporated herein by reference.

Preferably, the epoxidation is conducted by reacting the allyl ethers with a peroxygen compound such as peracetic acid or hydrogen peroxide in the presence of catalysts such as $Na_2WO_4/H_3PO_4$/quaternary ammonium salt such as, for example, trioctyl methyl ammonium nitrate. Both techniques are well-known in the art.

The hydrogen peroxide epoxidation is conducted at temperatures of from about 0° C. to about 100° C., preferably from about 20° C. to about 60° C., more preferably from about 35° C. to 50° C.

The peracetic acid epoxidation is conducted at temperatures of from about 20° C. to about 200° C., preferably from about 40° C. to about 100° C., more preferably from about 40° C. to about 80° C.

A highly preferred summary of the entire three-step process from propylene to epoxy resin is as follows:

1) Propylene+oxygen+acetic acid+catalyst → allyl acetate;
2) Allyl acetate+active hydrogen-containing compound such as bisphenol-A → diallyl derivative of active hydrogen-containing compound; and
3) Diallyl derivative of active hydrogen-containing compound+peroxy oxidant → diglycidyl derivative of active hydrogen-containing compound.

The epoxy resin made by the present invention preferably contains on average at least about one glycidyl ether, glycidyl thioether, or glycidyl ester group per molecule; more preferably contains on average more than one such group per molecule, and most preferably contains on average at least about 1.8 such groups per molecule. It preferably contains on average no more than about 10 such groups per molecule, more preferably no more than about 3 and most preferably no more than about 2.1. The functional groups are more preferably glycidyl ether or glycidyl ester groups, and are most preferably glycidyl ether groups. The epoxy or epoxide equivalent weight (EEW) is preferably at least about 100, more preferably at least about 150 and most preferably at least about 170. The EEW is preferably no more than about 200 and more preferably no more than about 1000. The resin contains less than 300 or 150 ppm, preferably less than about 50 ppm, more preferably less than about 30, and most preferably less than about 10 ppm total organic halogen. It optimally contains about 0 ppm total organic halogen. These amounts of "total organic halogen" exclude any halogen atoms attached to an aromatic ring to which the group containing the vicinal epoxide group is attached.

While theoretically, the process of the present invention which does not include the use of an epihalohydrin results in products totally free of any organic halogen, some organic halogen may be found in the product due to contamination of raw materials employed including, but not limited to solvents, active hydrogen-containing compounds, catalysts, bases, and the like.

The epoxy resins prepared by the process of the present invention are useful in such applications as, for example, electrodeposition and powder coatings, encapsulants, molding, casting, composites, laminates, adhesives and the like.

The epoxy resins prepared by the process of the present invention based on aromatic hydroxyl-containing compounds, particularly those based on cresol-formaldehyde novolac resins are particularly useful in the preparation of electrical laminates and encapsulated electronic components, cathodic electrodeposition and powder coatings since halogen atoms are-known to be undesirable components in epoxy resins used in these applications.

The following examples are illustrative of the invention, but are not to be construed as to affecting the scope thereof in any manner.

In the following examples, the amount of total halide is determined by digesting the sample with caustic (NaOH) and titrating with silver nitrate.

In the following examples, the epoxide equivalent weight (EEW) is determined by titration with an acid.

EXAMPLE 1

A. Preparation of bisphenol-A Diallyl Ether from bisphenol A and allyl acetate using a heterogeneous palladium catalyst.

To a mixture of 11.4 g (0.05 mole) of bisphenol-A, 0.1 g ($2.5 \times 10^{-5}$ equiv.) of 5 percent palladium on charcoal, 0.1 g ($2 \times 10^{-4}$ equiv.) of triphenyl phosphine, and 14.5 g (1.05 equiv.) of potassium carbonate in 30 ml of isopropanol under a nitrogen atmosphere is added 11.0 g (1.1 equiv.) of allyl acetate and the mixture stirred at 85° C. After 4 hrs, both thin-layer chromatography and liquid chromatography analysis show that the reaction is practically completed and show only one product peak. The catalyst turnover rate is calculated to be 500/hr.

Recovery of bisphenol-A diallyl ether

To the mixture prepared in A above, 30 ml of water and 100 ml of ethyl acetate are added. The mixture is filtered and the organic layer is separated, dried and concentrated in vacuo at 2 mm Hg and 50° C. to yield 15.3 g of a colorless oil representing a yield of 99.4 percent based on bisphenol-A. Both infrared (IR; with no OH absorption) and nuclear magnetic resonance (NMR; appearance of an appropriate quantity of corresponding allylic protons) spectra are consistent with the desired product of bisphenol-A diallyl ether.

B. Epoxidation of bisphenol-A diallyl ether

To a solution of 12.5 g of diallyl ether of bisphenol-A (40 mmole) and 3.2 g (0.0076 equiv.) of trioctylmethylammonium nitrate in 30 ml of toluene is added an aqueous solution of 2.6 g of sodium tungstate (0.008 equiv.), 1.6 g of phosphoric acid (0.016 equiv.) and 16 g (~2 equiv.) of 30% hydrogen peroxide in 32 ml of water (final pH of 2.05). The mixture is stirred at 40° C. and liquid chromatography is used to monitor the progress of the reaction. After 4 days, the reaction is stopped when total disappearance of the allyl ether and the formation of a new product peak are observed. The aqueous layer is separated, extracted twice with 20 ml portions of toluene. The organic reaction mixture is combined with the extracts, washed twice with 30 ml portions of water, and dried over potassium carbonate and then concentrated in vacuo resulting in 17.0 g of a brown oil.

This crude brown oil is passed through a column of 250 g of silica gel packed in 20 percent of acetone in hexane. Elution of this column with a gradient of 20–50 percent acetone in hexane yields 9.5 g of a light yellow oil. Spectral data (IR and NMR; NMR: absence of olefinic protons and appearance of epoxide protons) are consistent with the desired product (the diglycidyl ether of bisphenol A). Furthermore, both thin layer chromatography and liquid chromatography show identical retention times with an authentic material. Analysis shows that the product obtained contains 26 ppm of total chloride and has an epoxy equivalent weight of 182.

EXAMPLE 2

Preparation of bisphenol-A diallyl ether from bisphenol-A and allyl Acetate Using Homogeneous Palladium Catalyst To a glass reactor equipped with glass baffles under a nitrogen atmosphere is added a solution of 35.0 g (0.875 mol) of sodium hydroxide in 300 ml of water. Then 40 g of dry ice is gradually added until a pH of 10.5 is obtained. Then 45.6 g (0.2 mol, 0.4 equiv.) of bisphenol-A is added. After stirring for 20 min, the mixture is heated to 85° C. and 80.0 g (0.8 equiv.) of allyl acetate, 0.028 g ($1.25 \times 10^{-4}$ mole) of palladium acetate and 0.162 g ($0.3 \times 10^{-4}$ mole) of triphenyl phosphine are then added. After stirring rapidly (~600 rpm) for 15 min, the reaction is >99% complete and the liquid chromatogram shows cleanly one product peak. The stirring is stopped and the organic layer is separated and concentrated in vacuo to yield 58.61 g of desired product. The yield is 95.2%. The catalyst turnover rate is calculated to be 6400/hr.

Repeating the above example using a stirring rate of ~60 rpm instead of ~600 rpm the conversion was only 14.4% after 15 min.

EXAMPLE 3

A. Preparation Of Allyl Phenolic Novolac

To a mixture of 6.2 g (20 mmole) of cresol novolac (average M.W.=310, hydroxy equiv. wt.=~124, average functionality=2.5), 8.0 g (1.1 equiv.) of potassium carbonate, 50 mg ($1.1 \times 10^{-5}$ mole) of 5 percent palladium on charcoal, and 20 mg ($8 \times 10^{-31.5}$ mole) of triphenyl phosphine in 25 ml of isopropanol, is slowly added 6.0 g (0.06 mole) of allyl acetate. After the resultant mixture is stirred at 85° C. for 8 hr, liquid chromatography shows that the reaction is complete. Water (30 ml) and toluene (30 ml) are added to the mixture. After extracting, the toluene layer is separated and the aqueous layer is again extracted with another 30 ml of toluene. After separation, the toluene extracts are combined, dried over magnesium sulfate and concentrated in vacuo to a viscous pale yellow oil (7.8 g, ~95 percent yield). Spectral data of this material are consistent with the desired allylated product. The NMR spectrum shows the presence of the vinylic-H and the allylic-hydrogenes while the IR spectrum shows the absence of OH absorption.

B. Epoxidation of Allyl Phenol Novolac

An aqueous solution containing 2.65 g (0.008 mole) of sodium tungstate dihydrate, 1.6 g (0.016 mole) of phosphoric acid and 8.0 g (0.165 mole) of 70% hydrogen peroxide in 28 ml of water (mixture pH=2.05) is added to a 24 ml toluene solution containing 12.6 g (0.1 equiv.) of allylated cresol novolac prepared in A above and 1.6 g (0.0045 mole) of trioctylmethylammonium nitrate. The mixture is stirred at 45° C. for 28 hr and is stopped when almost all starting material has disappeared. The mixture is cooled and the organic layer separated and washed 3 times with 50 ml of water. It is then dried over magnesium sulfate, filtered and concentrated in vacuo to give 13.6 g of a viscous amber liquid.

To remove the ammonium nitrate from the crude product, the material is extracted with 5 ml of methanol by warming up with stirring, cooling to room temperature and decanting the extracting methanol. The process is repeated four times. The product is then concentrated with roto-evaporator (<100° C./2 mm Hg), yielding 9.1 g of desired cresol epoxy novolac {analysis: total organic Cl=1 ppm, % epoxide= 19.12% (EEW=224.9)}.

EXAMPLE 4

A. Allylation of Benzyl Alcohol

A mixture of benzyl alcohol (10.8 g, 0.1 mole), allyl acetate (10.5 g, 1.05 equiv.) and potassium carbonate (15 g, 0.109 mole) in 15 ml of water is stirred under nitrogen for 15 min. Then 10 mg ($4.46 \times 10^{-5}$ mole) of palladium acetate and 30 mg ($8.5 \times 10^{-31.5}$ mole) of triphenyl phosphine are added and the mixture is stirred at 85° C. After 48 hrs, the reaction is 65% completed and the reaction rate becomes quite sluggish. After cooling, 50 ml of water and 50 ml of toluene were added for extraction. The organic extract was separated and washed twice with 30 ml of water, dried over magnesium sulfate and concentrated in vacuo yielding 14.2 g. This light brown liquid is distilled and collected at 71–74° C./13 mm Hg, yielding 8.5 g of a colorless liquid (NMR and IR spectra are consistent with the desired benzyl allyl ether).

B. Epoxidation of Benzyl Allyl Ether

An aqueous solution containing 1.32 g (0.004 mole) of sodium tungstate dihydrate, 1.0 g (0.01 mole) of phosphoric acid and 12.5 g (0.12 mole) of 30% hydrogen peroxide in 18 ml of water (mixture pH=1.98) is added to a 24 ml toluene solution containing 8.5 g (0.063 mole) of benzyl allyl ether and 1.0 g (0.0023 mole) trioctylmethylammonium nitrate. The mixture is stirred at 45° C. for 36 hr and is stopped when almost all starting material has disappeared. The mixture is cooled and the organic layer is separated and washed three times with 50 ml of water. It is then dried over magnesium sulfate, filtered and concentrated in vacuo to give 12.2 g of a viscous amber liquid.

To remove the ammonium nitrate from the crude product, the material is chromatographed over 200 g of silica gel packed in 10% acetone in hexane. Elution of this column with a gradient of 10–20% acetone/hexane yields 8.2 g of material analyzed to have total organic chloride of 199 PPM and an EEW of 164.

EXAMPLE 5

A. Allylation of Methacrylic Acid

A mixture of methacrylic acid (17.2 g, 0.2 mole), allyl acetate (21.0 g, 1.05 equiv.) and potassium carbonate (30 g, 1.09 equiv.) in 30 ml of water is stirred under nitrogen for 15 min. Then 20 mg of palladium acetate ($4.46 \times 10^{-4}$ equiv.) and 60 mg ($8.5 \times 10^{-4}$ equiv.) of triphenyl phosphine are added and the mixture is stirred at 85° C. After 24 hr, gas chromatography shows the reaction is 55% converted and a major new peak is formed. Since further stirring and heating do not advance the reaction, it is stopped. After cooling, 100 ml of water and 100 ml of toluene are added for extraction. The organic extract is collected and washed twice with 30 ml of water, dried over magnesium sulfate and concentrated in vacuo yielding 21.2 g of product. This light brown liquid is distilled and collected at 48–51° C./32 mm Hg, yielding 11.6 g of a colorless liquid having identical gas chromatographic retention time as that of a commercial sample of allyl methacrylate.

B. Epoxidation of Allyl Methacrylate

An aqueous solution containing 1.32 g (0.004 mole), of sodium tungstate dihydrate 1.0 g (0.01 mole) of phosphoric acid and 12.5 g (0.12 mole) of 30% hydrogen peroxide in 18 ml of water (mixture pH=2.05) was added to a 24 ml toluene solution containing 7.5 g (0.06 mole) of allyl methaccrylate and 1.0 g (0.0023 equiv.) trioctylmethylammonium nitrate. The mixture was stirred at 45° C. for 30 hrs and was stopped when gas chromotrography showed that almost all starting material had disappeared and a major new peak having identical retention time as commercial glycidyl methacrylate had appeared. The mixture was cooled and the organic layer was separated and washed three time with 10 ml portions of water. It was then dried over magnesium sulfate, filtered and concentrated in vacuo to give 9.8 g of a viscous amber liquid.

EXAMPLE 6

A. Allylation of Aniline

A mixture of aniline (2.4 g, 25 mmole) potassium carbonate (8.0 g, 0.06 mole), 6.0 g (0.06 mole, 2.4 equiv.) of allyl acetate, 50 mg ($1.1 \times 10^{-5}$ mole) of palladium on charcoal and 20 mg ($8 \times 10^{-5}$ mole) of triphenyl phosphine in 25 ml of isopropanol is stirred for 22 hr. When gas chromatography shows the absence of the starting material and the appearance of a new peak indicating that the reaction is complete, water (20 ml) and ethyl acetate (40 ml) are added for extraction. The extract is dried and concentrated in vacuo to an amber oil of 3.5 g (78.7% yield) whose NMR spectrum is consistent with the structure of diallyl aniline.

What is claimed is:

1. A glycidyl ether, glycidyl amine or glycidyl thioether resin having an average of more than one vicinal epoxide group per molecule produced by:

(a) allylating one or more compounds containing at least one hydroxyl group, thiol group, or primary or secondary aromatic amine group per molecule with an allyl reagent which contains at least one allyl carboxylate group or allyl carbonate group, whereby an allyl ether, allyl amine or allyl thioether compound is formed; and (b) converting the allyl groups on the compound from (a) to epoxide groups, whereby a glycidyl ether, glycidyl amine or glycidyl thioether resin having an average of more than one vicinal epoxide group per molecule is formed; said glycidyl ether, glycidyl amine or glycidyl thioether resin having an average of more than one vicinal epoxide group per molecule also having an epoxide equivalent weight of less than about 300 and an amount of total organic halide of less than about 30 ppm excluding any halogen atoms attached to an aromatic ring to which the group containing the vicinal epoxide group is attached.

2. A resin of claim 1 which has an epoxide equivalent weight of less than about 195.

3. A resin of claim 1 which has an epoxide equivalent weight of less than about 190.

4. A resin of claim 1 which has an amount of total organic halide of less than about 10 ppm excluding any halogen atoms attached to an aromatic ring to which the group containing the vicinal epoxide group is attached.

5. A resin of claim 1 which does not contain any halogen atoms attached to an aromatic ring to which the group containing the vicinal epoxide group is attached.

6. A resin of claim 2 which does not contain any halogen atoms attached to an aromatic ring to which the group containing the vicinal epoxide group is attached.

7. A resin of claim 3 which does not contain any halogen atoms attached to an aromatic ring to which the group containing the vicinal epoxide group is attached.

8. A resin of claim 4 which does not contain any halogen atoms attached to an aromatic ring to which the group containing the vicinal epoxide group is attached.

* * * * *